United States Patent
Rubröder et al.

(10) Patent No.: US 6,734,164 B2
(45) Date of Patent: *May 11, 2004

(54) PROCESS FOR THE STABILIZATION OF PROTEINS IN COMPLEX MIXTURES DURING THEIR STORAGE IN AQUEOUS SOLVENTS

(75) Inventors: Franz-Josef Rubröder, Vilmar (DE); Reinhold Keller, Bad Soden (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/991,964

(22) Filed: Nov. 26, 2001

(65) Prior Publication Data

US 2002/0058623 A1 May 16, 2002

Related U.S. Application Data

(63) Continuation of application No. 09/608,297, filed on Jun. 30, 2000, now Pat. No. 6,339,061.

(30) Foreign Application Priority Data

Jul. 2, 1999 (DE) .......................... 199 30 676

(51) Int. Cl.[7] .................. A61K 38/28; A61K 38/00; C07K 14/82; C12N 1/21; C12N 15/63
(52) U.S. Cl. .................. 514/3; 514/2; 435/243; 435/252.33; 435/255.1; 435/255.2; 435/255.5; 435/320.1; 435/325; 435/348; 530/303
(58) Field of Search .................. 435/69.1, 252.33, 435/320.1, 255.1, 255.5, 325, 348, 243; 530/303, 324; 514/2, 3

(56) References Cited

U.S. PATENT DOCUMENTS

| 4,371,523 A | 2/1983 | Grodsky et al. ............ 424/178 |
| 4,937,085 A | 6/1990 | Cherry et al. ............... 426/269 |
| 5,227,293 A | 7/1993 | Stengelin et al. .......... 435/69.7 |
| 5,756,672 A | 5/1998 | Builder et al. .............. 530/350 |
| 5,986,048 A | 11/1999 | Rubröder et al. ........... 530/303 |

FOREIGN PATENT DOCUMENTS

| EP | 158487 | * 10/1985 | |
| EP | 0 195 691 A1 | 9/1986 | ........... C12N/15/00 |
| EP | 0 335 554 A2 | 10/1989 | ........... A61K/7/06 |
| EP | 0 437 622 A1 | 7/1991 | ........... A61K/37/24 |
| EP | 0 489 780 | 6/1998 | ........... C12N/15/00 |
| EP | 0 906 918 A2 | 4/1999 | ........... C07K/14/62 |
| WO | WO 93/11240 | 6/1993 | ........... C12N/15/16 |
| WO | WO 96/27661 | * 9/1996 | ........... C12N/9/96 |

OTHER PUBLICATIONS

Santha et al., 1979, Indian J. Anim. Sci., 49, 1, pp. 37–41.*
Ahmad et al., 1983, J. Am.Oil.Chem.Soc., 60, 4, pp. 837–840.*
W.D. Lougheed, et al. "Insulin Aggregation in Artificial Delivery Systems," *Diabetologia* 19:1–9 (1980).
H. Qi, et al. "Stability and stabilization of insulinotropin in a dextran formulation," Abstract No. 96148261, *PDA Journal of Pharmaceutical Science and Technology* 49(6):289–93 (1995).
P. Golini, et al. "Immobilization of D–Amino Acid Oxidase from Different Yeasts: Characterization and Application in the Deamination of Cephalosporin C" *Enzyme and Microbial Technology* 17:324–329 (1995).
W. Kordel, et al., "Chemical Investigations on Pig Kidney Aminoacylase," *Biochimica et Biophysica Acta*, 445:446–457 (1976).

* cited by examiner

*Primary Examiner*—John Ulm
*Assistant Examiner*—Olga N. Chernyshev
(74) *Attorney, Agent, or Firm*—Finnegan, Henderson, Farabow, Garrett & Dunner, L.L.P.

(57) ABSTRACT

The present invention relates to a process for the storage of proteins in an aqueous solution. The addition of cysteine delays the temporal decrease in the effective concentration of the protein. The process is suitable for use in the production of heterologous proteins in microorganisms.

6 Claims, No Drawings

US 6,734,164 B2

PROCESS FOR THE STABILIZATION OF PROTEINS IN COMPLEX MIXTURES DURING THEIR STORAGE IN AQUEOUS SOLVENTS

This is a continuation of application Ser. No. 091608, 297, filed Jun. 30, 2000 which claims priority to German Application No. 19930676.1, filed Jul. 2, 1999, both of which are incorporated herein by reference.

FIELD OF THE INVENTION

The present invention relates to a process for the storage of proteins in an aqueous solvent.

BACKGROUND OF THE INVENTION

The chemical state of the SH groups of proteins or other oxidation-sensitive structures often has an effect on the identity, activity, or effective concentration of proteins. Identity means the respective folding of a protein. Activity should be understood as meaning enzyme activity. The effective concentration of a protein should be the proportion of the protein in a solution, which is correctly folded with respect to the biological in vivo function.

It is known from the literature that structure-modifying oxidations of proteins can be suppressed by the use of thiol reagents such as, for example, 2-mercaptoethanol or cysteine.

For example, D-amino acid oxidase (DAO) can be stabilized by thiols. The flavoprotein DAO catalyzes the stereospecific deamination of D-amino acids to the corresponding α-ketoacids and ammonium (P. Golini et al., *Enzyme and Microbial Technology* 17:324–329 (1995)). However, the addition of thiols such as, for example, cysteine can also reduce the activity of proteins. This effect can also be explained by the presence of cysteine radicals. An example of this is aminoacylase. Aminoacylase is a dimeric enzyme having one $Zn^{2+}$ atom per subunit. Each subunit of the enzyme contains 2 cysteine SH groups and 2 disulfide bonds. The chemical modification of the SH groups, such as the breaking of the disulfide bonds, can lead to an inactivation of the enzyme. It was possible to show that, by the addition of 2-mercaptoethanol, the activity of the aminoacylase is reduced, whereas after removal of the 2-mercaptoethanol by dialysis or gel filtration the original enzyme activity can be almost completely restored (W. Ködel and F. Schneider, *Biochem. Biophys. Acta* 445:446–457 (1976)).

For cysteine and some derivatives, it was possible for certain preparation forms and specific applications to demonstrate an antibacterial, antiviral or antifungal activity to a certain extent. Thus, for example, it was possible to show that the addition of cysteine is suitable to a certain extent as protection against the spoilage of foods (U.S. Pat. No. 4,937,085).

With the aid of genetic engineering processes, it is possible to synthesize recombinant proteins, such as insulin or its precursors, and also insulin derivatives which have amino acid compositions differing from the derived gene sequence (e.g., human), in genetically modified microorganisms, such as the bacterium *Escherichia coli*.

Recombinant synthesis in microorganisms is carried out with the aid of expression vectors. These expression vectors consist of a vector plasmid containing a control sequence for the replication of the plasmid and a selection gene (inter alia, antibiotic resistance gene, metabolic marker). The coding region of the gene for the protein of interest (e.g., insulin) may be inserted under the control of a promoter that is active in the chosen microorganism. For example, if one chooses *E. coli*, the lac promoter may be used to control expression of the protein of interest.

A process for the production of recombinant proteins (e.g., insulin or insulin derivatives) with the cooperation of genetically modified microorganisms is composed of a series of process steps, which intermesh with each other and must be coordinated with one another.

Thus, for example, a process for the production of human insulin in *E. coli* can be constructed from the following process steps:

Fermentation of the microorganisms; cell separation; cell disruption; isolation and intermediate storage of the fusion protein with cysteine; refolding into the native spatial structure including formation of the correct disulfide bridges and subsequent separation of foreign proteins not containing material of value; enzymatic cleavage to the arginylinsulin; basic purification of the aqueous protein solution; $1^{st}$ chromatographic purification; enzymatic cleavage to human insulin; $2^{nd}$ chromatographic purification; high purification by means of HPLC; recrystallization; and drying.

The large number of individual steps carried out, as a rule, leads to a considerable loss in total yield, because losses in the specific yield of each individual process step are unavoidable.

By optimizing these intermediate steps, the total yield can be improved. There is considerable interest in such processes in order to improve economical utilization of the resources employed and to decrease environmental pollution.

For example, EP-0906918 describes an improved process for the production of a precursor of insulin or insulin derivatives having correctly linked cystine bridges in the presence of cysteine or cysteine hydrochloride and of a chaotropic auxiliary.

Insulin derivatives are derivatives of naturally occurring insulins, such as human insulin or animal insulins. These insulin derivatives differ from the naturally occurring insulin by the deletion, substitution, and/or addition of at least one genetically encodable amino acid residue in the naturally occurring insulin.

During the storage of proteins, a decrease in the effective concentration usually occurs.

The storage of production products between individual process steps may be necessary for various reasons. For example, a subsequent industrial processing step may not be able to accept the total amount of product of the preceding process step, thus requiring storage of a portion of the previous product.

The time needed for intermediate storage may be of differing length. Owing to capacity, the need to coordinate industrial units, the required delivery of more chemicals or appliances, or other reasons, it may be necessary to extend the intermediate storage to several weeks.

One effective way of increasing the yield of the final product is to reduce the loss of active protein that may occur during the unavoidable intermediate storage of products from individual process steps before further processing takes place.

The use of cysteine or its derivatives for the control of the potential loss in yield of active protein during intermediate storage of production products has not been described until now. These products can differ in composition, as well as in form, including biological components, for example, with participation of enzyme catalysts or genetically modified microorganisms. Such processes are used, for example, in the preparation of insulin.

Depending on the process step, the production products to be intermediately stored can consist of, inter alia, different amounts of complex macromolecules of a biological nature (e.g., proteins, DNA, fats), microorganisms, buffer substances, and starting materials.

The production process, as a rule, is aimed at the preparation of a substance that is as uniform as possible, e.g., the production of insulin from a genetically modified microorganism. If intermediate products have to be stored, e.g., in the preparation of insulin, loss of effective concentration of this protein regularly occurs.

Storage of a protein should be understood as meaning any storage of the protein, regardless of the volumetric amount in which the protein is present, the time period of the storage, or the temperature conditions under which the storage takes place. The storage of proteins normally takes place in aqueous solutions.

An aqueous solution of a protein may contain constituents of nutrient media for the culture of microorganisms in defined form or as a complete media containing, in particular, carbon sources or nitrogen sources, amino acids, inorganic salts, and trace elements. The aqueous solution may also contain buffer components of different chemical buffer types, as well as macromolecules of biological origin, such as DNA or fats. The aqueous solution may additionally contain organic or inorganic compounds such as, for example, sodium dodecylsulfate ("SDS") or potassium acetate, and also proportions of solvents of differing priority, such as methanol or petroleum ether.

SUMMARY OF THE INVENTION

The present invention relates to a process for the storage of a protein in an aqueous solution, which comprises delaying the temporal decrease in the effective concentration of the protein by the addition of cysteine to the aqueous solution.

The process is suitable for the stabilization of proteins during storage thereof. The addition of cysteine slows the temporal decrease in the effective concentration of a protein during its storage in aqueous solutions. The process can be used, for example, in the production of proteins by microorganisms. Examples of appropriate microorganisms are, inter alia, preferably bacteria, particularly *Escherichia coli*; yeasts, particularly *Saccharomyces cerevisiae* or *Pichia pastoris*. In addition, the production of proteins may be by insect cells. In the preferred embodiment, these microorganisms can be transformed using expression vector constructs for the induced or constitutive expression of said protein. The microorganisms are cultured and then disrupted after synthesis of the protein. Suitable disruption methods include all processes that are suitable for the release of the protein from the microorganism, for example, ultrasound, chemical methods using potassium acetate, SDS, or lysozyme, heating of the microorganisms, or the French press. The disruption of the microorganisms may be omitted if the protein to be prepared is secreted directly into the medium. In principle, the process is also applicable to extruded proteins.

The complex protein mixtures, which result when the microorganisms are disrupted or when the protein is extruded directly into the medium, are usually in aqueous solution. The proteins may be dissolved therein or present in suspended form. These protein solutions are preferably stored from about 0° C. to about 50° C. or from about 5° C. to about 30° C. or at about 5° C. To delay the inactivation of the protein of interest, cysteine is added to this protein mixture. The concentration of cysteine in the protein mixture may be between 100 and 500 mM or preferably between 150 and 220 mM. A concentration of 170 mM is more preferable. In this way, proteins in complex molecule solutions can be stored for up to several weeks with only a slight decrease in the effective protein concentration. The process is applicable to the synthesis of heterologous proteins, in particular in microorganisms, after their disruption with subsequent purification and possible renaturation, preferably for the preparation of insulin and its precursor.

Proteins used for storage in a process of the invention are preferably insulin or insulin derivatives.

The present invention further relates to a process for the preparation of a heterologous protein, comprising the expression of the heterologous protein or its precursor in a transformed microorganism. The heterologous protein is then stored by means of a process according to the present invention. This heterologous protein or a precursor thereof is optionally then renatured, purified of leader sequences or otherwise processed, and finally prepared to give the desired product after purification and isolation. Suitable heterologous proteins are preferably insulin or insulin derivatives, or precursors of insulin.

DETAILED DESCRIPTION OF THE INVENTION

During the implementation of the processes for the preparation of insulin, it was found that, by adding cysteine to the fusion protein, the product remained stable in storage for months. In comparison, the untreated product lost some of its activity irreversibly after just a few days.

The precursor molecules of human insulin or an insulin derivative were used in the following examples. The structure and amino acid sequence were disclosed in EP 906 918. The precursor of human insulin has the sequence of naturally occurring human insulin. The precursor of the insulin derivative contains a glycine instead of an arginine at position 21 of the A chain and two arginine molecules at positions 31 and 32 at the C-terminal end of the B chain.

Fusion proteins of the insulins can be prepared by fermentation of genetically modified *E. coli* cells according to EP 0 489 780 and EP 0 906 918. A protein suspension was obtained containing approximately 20 to 25% dry matter and 40 to 50% foldable insulin.

For the sought-after stabilization of the protein by means of cysteine, 75 kg of cysteine hydrochloride×$H_2O$ was introduced into about 2500 kg of this protein suspension (corresponding to one fermentation batch) over the course of 20 minutes with vigorous stirring. The pH fell from about 7.0 to about 2.5 during this process. The suspension became very pasty in the pH range around 5 and readily stirrable again from around pH 4. Under these experimental conditions, a cysteine hydrochloride concentration of about 170 mM was established in the protein suspension. The protein suspension was subsequently stirred for about 60 min., after which it remained without further stirring until working-up.

EXAMPLE 1

For experimental confirmation of the preserving action of cysteine, the following laboratory experiments were carried out:

A fusion protein of human insulin and a fusion protein of the insulin derivative prepared according to EP 906 918 were stored with and without cysteine at 5° C. and at room temperature for up to 2 months. During the experiment, aliquots were periodically removed from the batches. The fusion protein was converted into the prepro form of human insulin or prepro form of the insulin derivative by reductive folding (EP 906 918). The amount of cysteine necessary for folding was added to each batch that had been stored without cysteine hydrochloride monohydrate about 1 hour before the start of folding. In those batches containing cysteine in the form of the preservative, it was not necessary to add additional cysteine to obtain proper folding of the insulin molecule.

The prepro form of human insulin or prepro form of the insulin derivative was determined by means of HPLC.

HPLC Analysis 0.5 g of protein was dissolved in 40 ml of a solution containing 6 M guanidine hydrochloride, 50 mM TRIS, 5 mM ethylenediaminetetraacetate (EDTA) at pH 8.5, 1% 2-mercaptoethanol, and 10 mM dithiothreitol at 95° C. for 2 min and then centrifuged at 14,000 g for 20 min. 0.02 ml of the clear supernatant was applied to a high-pressure liquid chromatography column.

Column: Nucleogel® RP 300-5/46 (Macherey & Nagel, Aachen, Germany)
Gradient: buffer A: 0.1% trifluoroacetic acid (TFA) buffer B: 0.09% TFA in acetonitrile
Temperature: 55° C.
Total running time: 40 min.

The gradient was defined by the following amounts of buffer B after the corresponding running times: 10 min 25%, 12 min 60%, 13 min 90%, 15 min 100%.
Flow: 1 ml/min
Detection: 215 nm
Result of the Experiments

TABLE 1

Storage of fusion protein of human insulin at 5° C., valuable substance (mg/l) after folding (valuable substance means folded human insulin)

|  | 1st day | 1 week | 2 weeks | 4 weeks | 8 weeks |
|---|---|---|---|---|---|
| With cysteine | 850 | 831 | 867 | 845 | 825 |
| Without cysteine | 879 | 827 | 790 | 712 | 625 |

TABLE 2

Storage of fusion protein of human insulin at room temperature, valuable substance (mg/l) after folding

|  | 1st day | 1 week | 2 weeks | 4 weeks | 8 weeks |
|---|---|---|---|---|---|
| With cysteine | 792 | 817 | 800 | 785 | 790 |
| Without cysteine | 812 | 654 | 312 | %* | %* |

*Application not possible because of severe putrefaction processes

TABLE 3

Storage of fusion protein of the insulin derivative at 5° C., valuable substance (mg/l) after folding

|  | 1st day | 1 week | 2 weeks | 4 weeks | 8 weeks |
|---|---|---|---|---|---|
| With cysteine | 590 | 553 | 540 | 573 | 552 |
| Without cysteine | 612 | 580 | 549 | 518 | 404 |

TABLE 4

Storage of fusion protein of the insulin derivative at room temperature, valuable substance (mg/l) after folding

|  | 1st day | 1 week | 2 weeks | 4 weeks | 8 weeks |
|---|---|---|---|---|---|
| With cysteine | 643 | 667 | 680 | 649 | 653 |
| Without cysteine | 597 | 547 | 420 | 271 | %* |

*Application not possible because of severe putrefaction processes

The addition of cysteine or cysteine hydrochloride allowed storage times of up to 2 months without significant loss of activity.

What is claimed is:

1. A process for the storage of a protein in an aqueous solution, comprising adding an amount of cysteine effective to delay the temporal decrease in the effective concentration of the protein wherein the effective concentration does not decrease by more than about 7%, and wherein cysteine is added in a concentration of from about 100 mM to the aqueous solution.

2. The process as claimed in claim 1, wherein cysteine is added in a concentration of greater than 100 mM to the aqueous solution.

3. The process as claimed in claim 1, wherein the concentration of cysteine in the aqueous protein solution is in the range from about 100 mM to about 500 mM.

4. A process for the storage of a protein in an aqueous solution, comprising adding an amount of cysteine effective to delay the temporal decrease in the effective concentration of the protein during a period of greater than 24 hours, wherein cysteine is added in a concentration of from about 100 mM to the aqueous solution.

5. The process as claimed in claim 4, wherein cysteine is added in a concentration of greater than 100 mM to the aqueous solution.

6. The process as claimed in claim 4, wherein the concentration of cysteine in the aqueous protein solution is in the range from about 100 mM to about 500 mM.

* * * * *